(12) United States Patent
Klemm et al.

(10) Patent No.: US 11,266,114 B2
(45) Date of Patent: *Mar. 8, 2022

(54) PETUNIA PLANTS HAVING A SPOTTED FLOWER COLOR PATTERN

(71) Applicant: Klemm+Sohn GmbH & Co. KG, Stuttgart (DE)

(72) Inventors: Nils Klemm, Stuttgart (DE); Andrea Dohm, Pforzheim (DE); Ulrich Sander, Stuttgart (DE); Antonella Capo, Latina (IT)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 84 days.

This patent is subject to a terminal disclaimer.

(21) Appl. No.: 16/739,926

(22) Filed: Jan. 10, 2020

(65) Prior Publication Data

US 2020/0275625 A1    Sep. 3, 2020

Related U.S. Application Data

(63) Continuation of application No. 16/579,514, filed on Sep. 23, 2019, now Pat. No. 10,588,288, which is a continuation of application No. 15/895,447, filed on Feb. 13, 2018, now Pat. No. 10,462,991, which is a continuation of application No. 15/461,822, filed on Mar. 17, 2017, now Pat. No. 9,913,438.

(60) Provisional application No. 62/316,271, filed on Mar. 31, 2016.

(51) Int. Cl.
   *A01H 6/82* (2018.01)
   *A01H 5/02* (2018.01)
   *A01H 1/02* (2006.01)

(52) U.S. Cl.
   CPC ............... *A01H 6/824* (2018.05); *A01H 1/02* (2013.01); *A01H 5/02* (2013.01)

(58) Field of Classification Search
   CPC ..................................................... A01H 6/824
   See application file for complete search history.

(56) References Cited

U.S. PATENT DOCUMENTS

| | | | |
|---|---|---|---|
| PP21,673 P2 | 1/2011 | Dummen | |
| PP27,237 P2 * | 10/2016 | Klemm | A01H 5/02 Plt./356.1 |
| 9,913,438 B2 * | 3/2018 | Klemm | A01H 6/824 |
| 10,420,317 B2 | 9/2019 | Klemm et al. | |
| 10,462,991 B2 * | 11/2019 | Klemm | A01H 6/824 |
| 10,588,288 B1 * | 3/2020 | Klemm | A01H 6/824 |
| 2017/0196177 A1 | 7/2017 | Klemm et al. | |
| 2018/0177148 A1 | 6/2018 | Klemm et al. | |
| 2020/0060134 A1 | 2/2020 | Klemm et al. | |

OTHER PUBLICATIONS

The Current vol. 6, No. 134, pp. 27 Matthews and McGovern editors. (Year: 1886).*
Atkinson et al, "Post-transcriptional silencing of chalcone synthase in petunia using a geminivirus-based episomal vector," The Plant Journal 15(5): 593-604 (1998).
The Current, vol. 6, No. 134, p. 27, Matthews and McGovern editors (1886).

* cited by examiner

*Primary Examiner* — David H Kruse
(74) *Attorney, Agent, or Firm* — Cooley LLP

(57) ABSTRACT

*Petunia* plants comprising spotted flower color patterns are disclosed. *Petunia* plants comprising spotted flower color patterns in combination with other flower patterns are also disclosed. Also disclosed are methods of breeding with the *Petunia* plants having the novel spotted flower color pattern to provide new, distinct and stable *Petunia* plants having flowers with a spotted flower color pattern.

19 Claims, 6 Drawing Sheets
Specification includes a Sequence Listing.

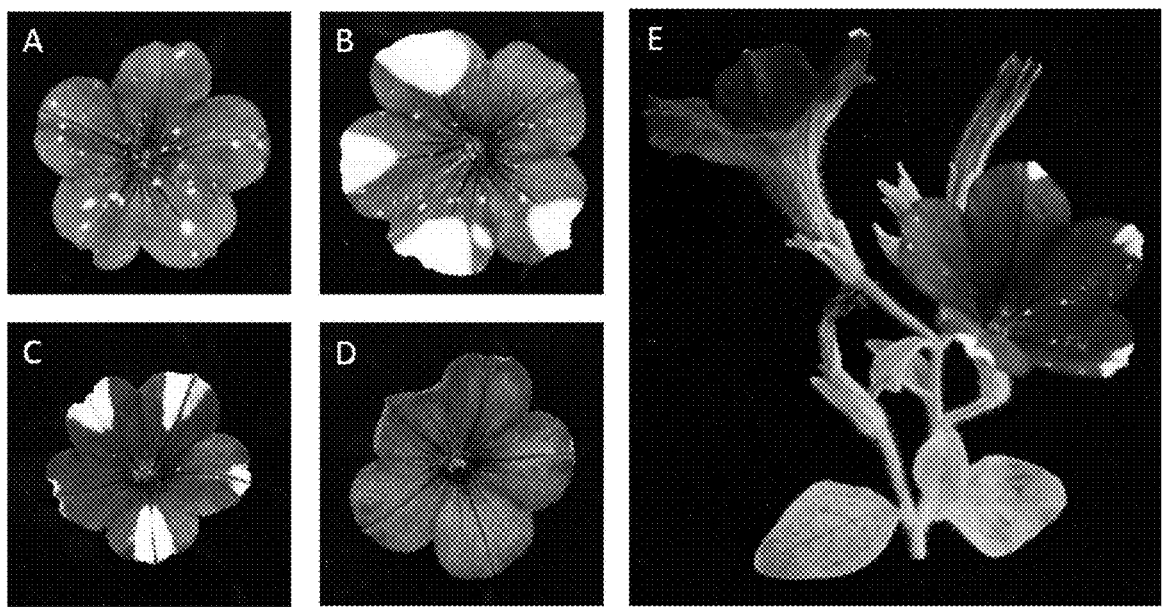
FIGs. 9A-9E
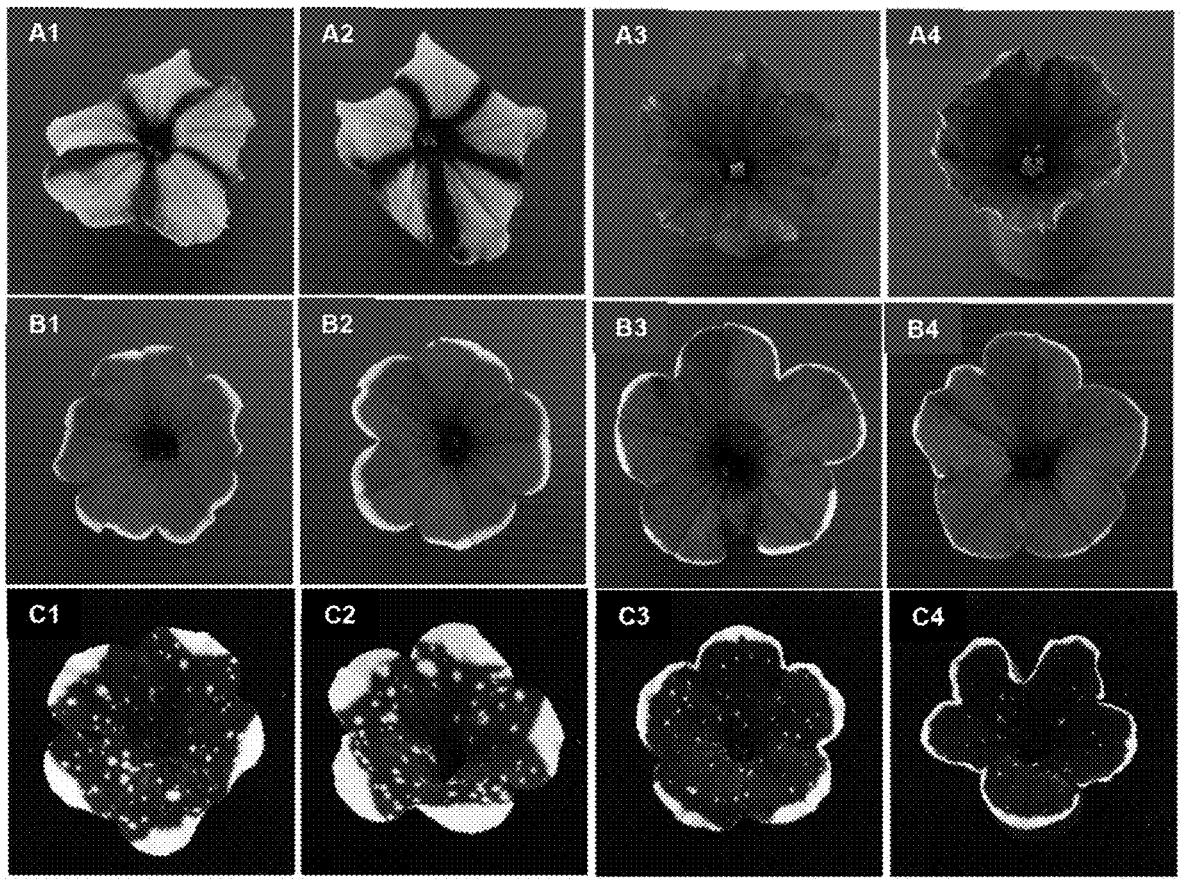
FIGs. 10A1-10C4

PETUNIA PLANTS HAVING A SPOTTED FLOWER COLOR PATTERN

CROSS-REFERENCE TO RELATED APPLICATIONS

The present application is a continuation application of U.S. application Ser. No. 16/579,514, filed Sep. 23, 2019, which is a continuation of U.S. application Ser. No. 15/895,447, filed Feb. 13, 2018, now issued as U.S. Pat. No. 10,462,991, which is itself a continuation of U.S. application Ser. No. 15/461,822, filed Mar. 17, 2017, now issued as U.S. Pat. No. 9,913,438, which claims priority to U.S. Provisional Application No. 62/316,271 filed on Mar. 31, 2016, the contents of each of which are hereby incorporated in their entirety.

SUBMISSION OF SEQUENCE LISTING

The Sequence Listing associated with this application is filed in electronic format via EFS-Web and is hereby incorporated by reference into the specification in its entirety.

BACKGROUND

All publications cited in this application are herein incorporated by reference. The present disclosure relates to the field of ornamental *Petunia* plants and plant breeding. The disclosure provides new, distinct and stable *Petunia* plants having inflorescences with a unique spotted flower color pattern. This color pattern has not been observed in any known *Petunia*, but was discovered through the Applicant's breeding program.

The genus *Petunia* belongs to the plant family Solanaceae and is divided into 14 different species, which are endemic to South America. The geographical distribution includes temperate and subtropical regions of Argentina, Uruguay, Bolivia, and Brazil, with a center of diversification in southern Brazil. The common garden *Petunia*, *Petunia x hybrida* (Hook.) Vilm, now commonly known as *Petunia hybrid*, is derived from a cross of the two species *P. integrifolia* and *P. axillaris*. The garden *Petunia* was first obtained through hybridization in 1834 by Atkins of Northhampton, a British nurseryman, and it soon spread to all European gardens (Sink, K. C. Ed. (1984) In: *Petunia*: Monographs on Theoretical and Applied Genetics 9. Springer-Verlag, Berlin, pp. 3-9). Today, it is used worldwide as an outdoor pot plant, in window boxes or as a bedding plant and is one of the most important ornamental plants. In 1983, Wijsman showed that crosses between further *Petunia* species as well as between the garden *Petunia* and other species are possible ((Wijsman, H. J. W. (1983). On the interrelationships of certain species of *Petunia*. II. Experimental data: Crosses between different taxa. *Acta Bot. Neerl.* 32:97-107; Wijsman, H. J. W. and Jong J. H. (1985) On the interrelationships of certain species of *Petunia*. IV. Hybridization and nomenclatural consequences in the *Petunia* group. *Acta Bot. Neerl.* 34: 337-349). Therefore, it is probable that further *Petunia* species have contributed to the modern varieties.

In commercial *Petunia* breeding, there has always been big interest in the development of new flower colors and color patterns, the modern *Petunia* varieties today cover a broad range of different flower colors as well as combinations therefrom. The flower color of *Petunia* is determined mainly by flavonoids, whereas the related species *Calibrachoa* uses anthocyanidins as well as carotenoids for the red flower color (Murakami, Y., Fukui, Y. Watanabe, H., Kokubun, H., Toya, Y. and T. Ando (2004) Floral coloration and pigmentation in *Calibrachoa* cultivars. *Journal of Horticultural Science & Biotechnology*, 79(1): 47-53). The basic chromosome number of the genus *Petunia* is seven; by this characteristic, as well as by further morphological traits, *Petunia* can be differentiated from *Calibrachoa* (Joao Renato Stehmann, Aline P. Lorenz-Lemke, Loreta B. Freitas and Joao Semir (2000) The Genus *Petunia*. In: T. Gerats and J. Strommer (Eds.), *Petunia*—Evolutionary, Developmental and Physiological Genetics. Second edition, Springer Verlag, Berlin, pp. 1-28), but the two genera can be intercrossed.

*Petunia* can be propagated from seed, cuttings, and tissue culture. Germination, cutting propagation, and tissue culture protocols for *Petunia* are well-known in the art.

*Petunia* is an important and valuable ornamental plant. Thus, a continuing goal of ornamental plant breeders is to develop plants with novel characteristics, such as color, growth habit, and hardiness. To accomplish this goal, the breeder must select and develop plants that have traits that result in superior *Petunia* varieties.

The foregoing examples of the related art and limitations related therewith are intended to be illustrative and not exclusive. Other limitations of the related art will become apparent to those of skill in the art upon a reading of the specification.

BRIEF DESCRIPTION OF THE FIGURES

The accompanying figures, which are incorporated herein and form a part of the specification, illustrate some, but not the only or exclusive, example embodiments and/or features. It is intended that the embodiments and figures disclosed herein are to be considered illustrative rather than limiting.

The patent or application file may contain one or more drawings executed in color and/or one or more photographs. Copies of this patent or patent application publication with color drawing(s) and/or photograph(s) will be provided by the Patent Office upon request and payment of the necessary fee.

FIGS. 9A-9E show that flower coloring of *Petunia* x *hybrida* variety 'KLEPH15313' infected with CMV can lead to changes in flower coloring. Flowers of this variety are originally purple with either white dots (A) or white petal tips and dots (B), which can be altered in infected plants to contain a purple smear in the white petal tips with vanishing white dots (C) and even to completely purple flowers (D). Only the clone PV-0036 also led to leaf symptoms with dark green dots on light green leaves (E).

FIGS. 10A1-10C4 show flower coloring of *Petunia* x *hybrida* lines showing different flower color patterns with and without CMV infection: line 'PH-2014-0028' uninfected (10A1 and 10A2) and infected (10A3 and 10A4); line 'PH-2007-0103' uninfected (10B1 and 10B2) and infected (10B3 and 10B4); line 'PH-2015-1874' infected (10C1 and 10C2) and uninfected (10C3 and 10C4).

SUMMARY

Figure 1:
FIG. 1 is a photo of the *Petunia* plant commercially designated 'KLEPH15313' showing the novel spotted flower color pattern, disclosed in the present application. The novel spotted flower color pattern consists of white spots on a purple base flower color.

The following embodiments and aspects thereof are described in conjunction with systems, tools and methods which are meant to be exemplary, not limiting in scope. In various embodiments, one or more of the above-described problems have been reduced or eliminated, while other embodiments are directed to other improvements.

According to one embodiment, there is provided a *Petunia* plant comprising at least one dominant allele that produces a spotted flower color pattern, wherein said spotted flower color pattern comprises having one or more spots on at least one petal, wherein a sample of representative seed of said *Petunia* plant comprising at least one dominant allele that produces a spotted flower color pattern. A further embodiment relates to said *Petunia* plant having said spotted flower color pattern that was deposited under NCIMB No. 42563. A further embodiment relates to wherein said spots may be white, cream, yellow, yellow-green, or combinations thereof in color. A further embodiment relates to wherein said spots may be circular or irregular in shape and may also vary in size. A further embodiment relates to wherein said *Petunia* plant showing said spotted color pattern may have a flower color of yellow, orange, red, brown, blue, black, pink, violet, or combinations and shades thereof. A further embodiment relates to wherein said *Petunia* plant having said spotted flower color pattern is in combination with a different flower pattern comprising a star pattern, a border pattern, or a star pattern and a border pattern. A further embodiment relates to wherein said *Petunia* plant showing having said spotted flower color pattern has a mature flower size between 2.5 cm and 10.5 cm.

Another embodiment relates to tissue culture produced from tissue, callus, or cells from the *Petunia* plants disclosed in the subject application, wherein said tissue, callus, or cells are produced from a plant part selected from the group consisting of: pollen, ovules, embryos, protoplasts, meristematic cells, callus, leaves, anthers, cotyledons, hypocotyl, pistils, roots, root tips, flowers, seeds, petiole, and stems.

Another embodiment relates to a method for producing *Petunia* seed, said method comprising crossing two *Petunia* plants and harvesting the resultant *Petunia* seed, wherein at least one *Petunia* plant is a *Petunia* plant having the spotted flower color pattern. A further embodiment relates to planting and growing the seed from said above cross to produce a *Petunia* plant having the spotted flower color pattern.

Another embodiment relates to a method of vegetatively propagating a *Petunia* plant of in the instant application comprising the steps of: (a) collecting tissue capable of being propagated from the plant according to a *Petunia* plant of in the instant application; (b) cultivating said tissue to obtain proliferated shoots; and (c) rooting said proliferated shoots to obtain rooted plantlets.

Another embodiment relates to a *Petunia* plant having a novel spotted flower color pattern, wherein said spotted flower color pattern comprises a *Petunia* plant having at least one flower having one or more spots on at least one petal, and wherein said pattern is produced from a post-transcriptional gene silencing of the Chalcone Synthase A gene in single randomly distributed cells of the petals. A further embodiment relates to wherein said spots may be white, cream, yellow, yellow-green, or combinations thereof in color. A further embodiment relates to wherein said spots may be circular or irregular in shape and may also vary in size. A further embodiment relates to wherein said *Petunia* plant showing said spotted color pattern may have a flower color of yellow, orange, red, brown, blue, black, pink, violet, or combinations and shades thereof. A further embodiment relates to wherein said *Petunia* plant having said spotted flower color pattern has in combination with a different flower pattern comprising a star pattern, a border pattern, or a star pattern and a border pattern. A further embodiment relates to wherein said *Petunia* plant having said spotted flower color pattern has a mature flower size between 2.5 cm and 10.5 cm.

In addition to the exemplary aspects and embodiments described above, further aspects and embodiments will become apparent by study of the following descriptions.

BRIEF DESCRIPTION OF THE SEQUENCE LISTINGS

SEQ ID NO:1 discloses the *Petunia* x *hybrida* primer CHSA-for (forward).

SEQ ID NO:2 discloses the *Petunia* x *hybrida* primer CHSA-rev (reverse).

Definitions

In the description and tables herein, a number of terms are used. In order to provide a clear and consistent understanding of the specification and claims, including the scope to be given such terms, the following definitions are provided:

Allele. Allele is any of one or more alternative forms for a gene.

Border Pattern. A "border pattern" refers to a pattern expressed on the flower where the color along the outer margin of the flower is different from the color of the rest of the flower. The color of the border along the outer margin of the flower may be thick or thin and solid or semi-solid. The color of the border along the outer margin and the rest of the flower may also vary in all colors and border patterns. Color, as referred to here, includes all pigmented colors and shades in-between, white, and unpigmented.

Gene. As used herein, "gene" refers to a segment of nucleic acid.

Locus. A locus is the position or location of a gene on a chromosome.

Progeny. As used herein, the descendants of one or more of the parental lines and includes an $F_1$ Petunia plant produced from the cross of two Petunia plants where at least one plant includes a Petunia plant disclosed herein and progeny further includes, but is not limited to, subsequent $F_2$, $F_3$, $F_4$, $F_5$, $F_6$, $F_7$, $F_8$, $F_9$, and $F_{10}$ generational crosses with the recurrent parental line.

RHS. RHS refers to the acronym for Royal Horticultural Society that publishes a color chart used in the plant industry. All RHS colors referred to herein are from the RHS 2007 edition.

Spotted Flower Color Pattern. As used herein, "spotted flower color pattern" refers to a pattern expressed as one or more spots on at least one petal of the flower. The spots range in shape from circular to irregular, vary in size, and vary in color from white, yellow, yellow-green, cream and combinations thereof.

Star Pattern. A "star pattern" refers to a pattern expressed on the flower where streaks of color longitudinally divide the pigmented sections of the flower. The streaks are sometimes referred to as lines and may be thin or thick and solid or semi-solid. The streaks or lines radiate from the center or approximately the center of the flower towards the outer margin of the flower. The streaks or lines may radiate all the way to the outer margin of the flower or partially towards the outer margin of the flower. The streaks or lines may vary in color and color patterns.

DETAILED DESCRIPTION

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possesses the traits to meet the program goals. The goal is to combine improved combination of desirable traits from the parental germplasm. These important traits may include flower color, certain plant characteristics, higher vigor, resistance to diseases and insects, better stems and roots, tolerance to drought and heat, and better commercial plant and flower quality.

According to one embodiment, there is provided a Petunia plant comprising at least one dominant allele that produces a spotted flower color pattern, wherein said spotted flower color pattern comprises having one or more spots on at least one petal, wherein a sample of representative seed of said Petunia plant comprising at least one dominant allele that produces a spotted flower color pattern is deposited under NCIMB No. 42563. A further embodiment relates to said Petunia plant and wherein said spots may be white, cream, yellow, yellow-green, or combinations thereof in color. A further embodiment relates to wherein said spots may be circular or irregular in shape and may also vary in size. A further embodiment relates to said Petunia plant and wherein said Petunia plant showing said spotted color pattern may have a flower color of yellow, orange, red, brown, blue, black, pink, violet, or combinations and shades thereof. A further embodiment relates to said Petunia plant and wherein said Petunia plant having said spotted flower color pattern has in combination with a different flower pattern comprising a star pattern or a border pattern. A further embodiment relates to said Petunia plant and wherein said Petunia plant having said spotted flower color pattern has a mature flower size between 2.5 cm and 10.5 cm.

The unique spotted flower color pattern comprises spots of a different color than the basic color of the respective flower.

A further embodiment relates to a Petunia plant comprising at least one dominant allele that produces a spotted flower color pattern, wherein said spotted flower color pattern comprises a Petunia plant having at least one flower having one or more spots on at least one petal, wherein a sample of representative seed of said Petunia plant comprising said at least one dominant allele that produces a spotted flower color pattern is deposited under NCIMB No. 42563.

The Petunia plants having a spotted flower color pattern disclosed in the present application have shown uniformity and stability, as described in the following section. The Petunia plants having a spotted flower color pattern disclosed in the present application have been asexually and sexually reproduced a sufficient number of generations with careful attention to uniformity of plant type and has been increased with continued observation for uniformity.

Origin of the Spotted Flower Color Pattern in Petunia

The unique spotted flower color pattern on Petunia flowers is the result of the Applicant's professional breeding program.

In 2010, a first cross was made between the P. grandiflorum seed variety 'Can Can' with the garden Petunia variety 'Veranda Navy Blue'. Further, a second cross was made between the variety 'Can Can' with the proprietary variety FAMOUS 'Dark Blue' ('KLEPH08153'). The varieties FAMOUS 'Dark Blue' and 'Veranda Navy Blue' both were solid-colored blue in flower color, whereas the flowers of the variety 'Can Can' showed a white center on a burgundy basic flower color. From the resulting progenies of each cross, Applicant selected two seedlings, one from each cross, and designated the seedlings 'PH-2011-2636' and 'PH-2011-2629'. Both seedlings displayed flower colors having a white center and a purple border. 'PH-2011-2636' and 'PH-2011-2629' were crossed in 2011, and in 2012, a single seedling, 'PH-2012-3528' was selected from the progeny population of that cross, which was the first seedling showing the novel spotted flower color pattern.

EXAMPLES

1. Genetic Background and Segregation Pattern

From 2012-2016, 155 crosses involving the spotted flower color pattern were performed in total, from which 25,248 seedlings were germinated and evaluated (please see Table 1). In Table 1 below, column one shows the year that the crosses were conducted, column two shows the total number of crosses conducted during that year, column three shows the total number of potted seedlings as a result of all of the crosses conducted during that year, column four shows the average number of progeny per cross (column 3 number divided by column 2 number), column five shows the minimum number of progeny observed from a given cross for that year, and column six shows the maximum number of progeny observed from a given cross that year.

Data in Table 1 comprises only those progenies, of which at least one parent expressed the spotted color flower pattern.

The progenies comprised on average 163 seedlings, whereas the number of the individual progenies varied from minimum of 1 to 493 seedlings (please see Table 1). Among the 155 individual crosses, not all of the seedlings from each cross showed the novel spotted flower color pattern, but every population showed at least one spotted seedling. Based on this observation, it is postulated that the inheritance of the novel *Petunia* spotted flower color pattern is dominant. However, the segregation patterns indicate that the dominance is incomplete and potentially, more than one gene is involved.

TABLE 1

Number of crosses with plants showing the novel spotted color pattern and population size of the resulting progenies

| Year | Crosses (total number) | Potted seedlings (total number) | Average number of progeny | Min. number of progeny observed | Max. number of progeny observed |
|---|---|---|---|---|---|
| 2012 | 9 | 1590 | 177 | 75 | 208 |
| 2013 | 9 | 660 | 73 | 30 | 90 |
| 2014 | 35 | 10986 | 314 | 4 | 493 |
| 2015 | 36 | 6404 | 178 | 2 | 397 |
| 2016 | 66 | 5608 | 85 | 1 | 208 |
| Total | 155 | 25248 | 163 | | |

Table 2 shows an overview of the proprietary breeding lines and commercial varieties which were used as parental lines in crosses to produce the seedling progenies in Table 1. The novel spotted flower color pattern was bred into a broad range of different flower colors, flower shapes, flower sizes, and growing habits. A number of both proprietary and commercial varieties were used as parental lines. Lines in column one indicate those lines proprietary to Applicant; those lines in column two third-party commercial lines.

TABLE 2

Parental lines crossed with spotted *Petunia* parental line to produce spotted *Petunia* progeny

| Applicant/proprietary variety used as crossing parent | Third party commercial variety used as parent crossing |
|---|---|
| ALPE TUNIA 'Dark Blue' | 'Sunshine Ray' |
| BONNIE 'Magenta' | POTUNIA 'Cobalt Blue 2016' |
| BONNIE 'Red '14' | POTUNIA 'Red 2016' |
| FAMOUS 'Blue' | SURPRISE 'Marine' |
| FAMOUS 'Dark Violet Picotee' | SURPRISE 'Midnight Blue' |
| FAMOUS 'Electric Orange' | SURPRISE 'Midnight Cowboy' |
| FAMOUS 'Electric Purple' | Sweetunia 'Hot Rod Red' |
| FAMOUS 'Purple evol.' | 'Viva Bright Red' |
| FAMOUS 'Red Fire '14' | ALPE TUNIA 'Dark Purple' |
| 'Lilac Picotee' | SURFINIA 'Early Light Yellow' |
| 'PH-2011-2416' | SURFINIA 'Early Pat Red' |
| 'PH-2012-306' | SURFINIA 'Purple' |
| 'PH-2013-4154' | SURFINIA 'Star Deep Violet' |
| 'PH-2013-4155' | SURFINIA 'Star Peach' |
| 'PH-2013-4258' | SURFINIA 'Star Purple' |
| 'PH-2013-4273' | SURFINIA 'Star Rose' |
| 'PH-2013-4277' | SURFINIA 'Star Violet' |
| 'PH-2013-4373' | SURFINIA 'Table Dark Red' |
| 'PH-2014-0004' | SURFINIA 'Violet' |
| 'PH-2014-0035' | SURFINIA 'Violet 2006' |
| 'PH-2014-0237' | SANGUNA 'Patio Red' |
| 'PH-2014-0594' | SANGUNA 'Purple Edge' |
| 'PH-2014-0756' | SANGUNA 'Purple Picotee' |
| 'PH-2014-0797' | |
| 'PH-2014-1019' | |
| 'PH-2015-1153' | |

Figure 2:
FIG. 2 is a photo showing a close-up of an individual flower of the plant shown in FIG. 1.

2. Breeding of 'KLEPH15313' (Also Commercially Known as 'KLEPH15313' *Petunia*, (FIGS. 1 and 2)

*Petunia* line 'KLEPH15313' is the result of a planned breeding program. 'KLEPH15313' was selected from a cross between 'PH-2012-3528', which was the first seedling discovered by Applicant showing the novel spotted flower color pattern and the variety 'Duesurmar', which has solid-colored blue flowers. The variety 'KLEPH15313' is a medium-compact, semi-spreading and cold tolerant *Petunia* plant, which displays the unique spotted flower color pattern. In FIG. 1, a whole plant of 'KLEPH15313' is depicted showing the spotted flower color pattern on all of the flowers of the plant. FIG. 2 depicts a close-up of a flower from FIG. 1 showing the spotted flower color pattern. In this example, the spotted flower color pattern shown is white spots on a purple base flower color. The spots vary from circular to irregular shape, vary in size, and are present on at least one petal of the flower.

3. Breeding of the Line 'PH-2015-1074' (FIG. 3)

*Petunia* line 'PH-2015-1074' displays petals having the spotted flower color pattern of white spots on a red base flower color, and is the result of a planned breeding program. In 2012, 'PH-2012-3528', which was the first seedling discovered by Applicant showing the novel spotted flower color pattern, was crossed with a proprietary *Petunia* seedling designated 'PH-2011-2416', which had solid-red colored flowers. The resulting progeny from this cross, 'PH-2013-4407', displayed purple flowers with a white spotted flower color pattern. 'PH-2013-4407' was further crossed with a solid black colored commercial variety named 'Surprise Midnight Cowboy' ('Duesurmidco'). Among the progeny of this last cross, a single seedling designated 'PH-2014-0009' was selected which displayed purple flowers with a yellow spotted flower color pattern. A further cross of 'PH-2014-0009' with a proprietary *Petunia* seedling designated 'PH-2014-0797' that does not have the spotted flower color pattern produced the line designated 'PH-2015-1074' having a white spotted flower color pattern with a red petal base color, as shown in FIG. 3.

Figure 3:
FIG. 3 is a photo showing a close-up of an individual flower of proprietary *Petunia* line 'PH-2015-1074' showing white spots on a red petal color.

As shown in FIG. 3, the spots vary from circular to irregular shape, vary in size, and are present on at least one petal of the flower.

4. Breeding of the Line 'PH-2015-1065' (FIG. 4)

*Petunia* line 'PH-2015-1065', which displays petals having a yellow-green spotted flower color pattern in combination with a yellow-green star pattern on a red-purple base petal color, is the result of a planned breeding program. In 2012, PH-2012-3528', which was the first seedling discovered by Applicant showing the novel spotted flower color pattern, was crossed with a proprietary seedling designed 'PH-2011-2416', which had solid-red flowers. The resulting progeny from this cross, 'PH-2013-4407' displayed purple flowers having a white spotted flower color pattern. 'PH-2013-4407' was further crossed with the solid black flower colored commercial variety 'Surprise Midnight Cowboy' ('Duesurmidco'). Among the progeny of this cross, 'PH-2014-0040' was selected which displayed dark-burgundy flowers with yellow spots. 'PH-2014-0040' was further crossed with a proprietary *Petunia* seedling designated 'PH-2014-1019', which also had solid-black flowers, to produce the line designated 'PH-2015-1065', which has a yellow-green spotted flower color pattern in combination with a yellow-greenish star pattern on a base red-purple petal color, as shown in FIG. 4.

Figure 4:
FIG. 4 is a photo showing a close-up of an individual flower of proprietary *Petunia* line 'PH-2015-1065' showing yellow-green spots in combination with a yellow-green star pattern on a base red-purple petal color

As shown in FIG. 4, the spots vary from circular to irregular shape, vary in size, and are present on at least one petal of the flower.

5. Breeding of the Line 'PH-2016-2150' (FIG. 5)

Figure 5:
FIG. 5 is a photo showing a close-up of an individual flower of proprietary *Petunia* line 'PH-2016-2150' showing flowers having a cream-yellow spotted flower color pattern in combination with a cream-yellow star pattern on a dark violet base flower color. This photo is an example of the spotted flower color pattern in combination with a border pattern and a star pattern.

*Petunia* line 'PH-2016-2150', as shown in FIG. 5, shows flowers having a cream-yellow spotted flower color pattern in combination with a cream-yellow star pattern on a dark violet base flower color. This photo is an example of the spotted flower color pattern in combination with a border pattern and a star pattern. and is the result of a planned breeding program. *Petunia* seedling 'PH-2016-2150' was selected in January 2016 among progeny from a cross between two proprietary seedlings, 'PH-2015-1118' and 'PH-2015-1132', both of which have flowers with a cream-yellow spotted flower color pattern on a dark-violet base petal color. 'PH-2015-1118' and 'PH-2015-1132' are derived from the progeny of the third filial cross of the proprietary *Petunia* seedling 'PH-2012-3528', which was the first seedling discovered by Applicant showing the novel spotted flower color pattern, with proprietary and commercial variety FAMOUS 'Dark Blue' ('KLEPH08153'), which has solid-blue flowers.

As shown in FIG. 5, the spots vary from circular to irregular shape, vary in size, and are present on at least one petal of the flower.

6. Breeding of the Line 'PH-2015-1874' (FIG. 6)

Figure 6:
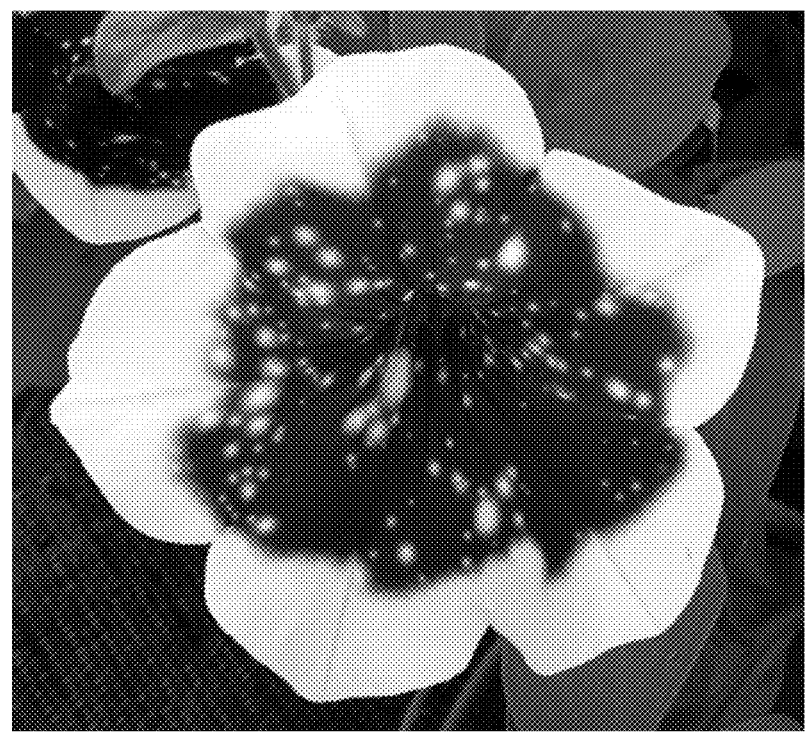
FIG. 6 is a photo showing a close-up of an individual flower of proprietary *Petunia* line 'PH-2015-1874' showing white spots in combination with a white border on a blue base petal color. This photo is an example of a flower with a solid border pattern in combination with the spotted flower color pattern of the present application.

*Petunia* line 'PH-2015-1874', as shown in FIG. 6, showing white spots in combination with a white border on a blue base petal color. This photo is an example of a flower with a solid border pattern in combination with the spotted flower color pattern of the present application, and is the result of a planned breeding program. 'PH-2015-1874' was selected in 2015 from a cross between the proprietary variety FAMOUS 'Dark Violet Picotee' ('KLEPH14250') and the proprietary *Petunia* variety 'KLEPH15313' (also commercially known as NIGHT SKY *Petunia* and shown in FIGS. 1 and 2). Whereas the female parent FAMOUS 'Dark Violet Picotee' ('KLEPH14250') displays dark-violet flowers with a white border, the flowers of the male parent 'KLEPH15313', display a white spotted flower color pattern on a purple base flower color.

As shown in FIG. 6, the spots vary from circular to irregular shape, vary in size, and are present on at least one petal of the flower.

7. Breeding of the Line 'PH-2016-2068' (FIG. 7)

Figure 7:
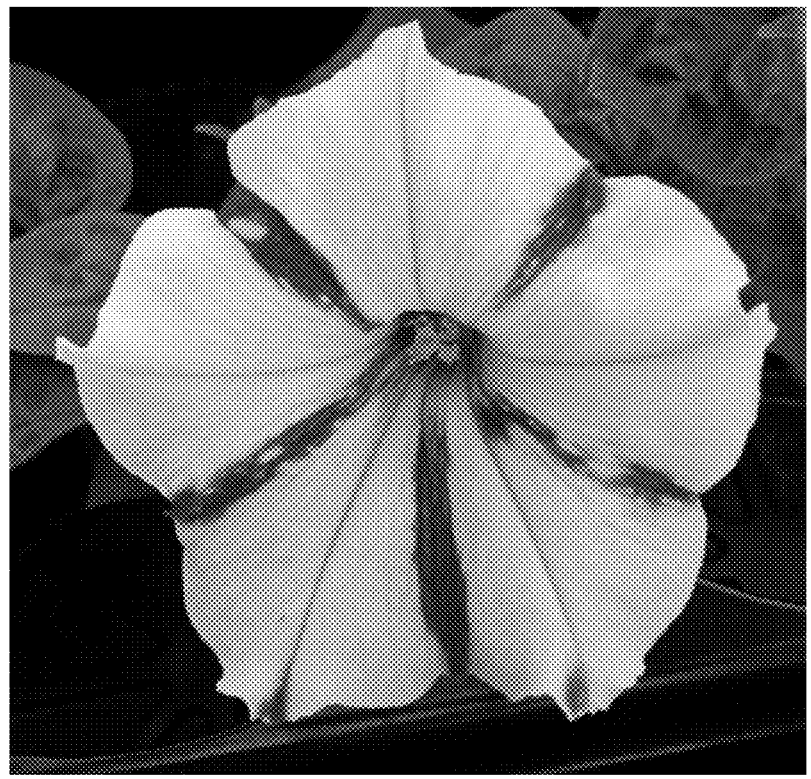
FIG. 7 is a photo showing a close-up of an individual flower of proprietary *Petunia* line 'PH-2016-2068' showing white spots on red star pattern in combination with a white base petal color.

*Petunia* line 'PH-2016-2068', as shown in FIG. 7, displays flowers having a white spotted flower color pattern on red star pattern in combination with a white base flower color and is the result of a planned breeding program. In 2012, PH-2012-3528', which was the first seedling discovered by Applicant showing the novel spotted flower color pattern, was crossed with the proprietary *Petunia* seedling 'PH-2011-2416', which had solid-red flowers. The resulting progeny from this cross, 'PH-2013-4407', displayed purple flowers with a white spotted flower color pattern. 'PH-2013-4407' was further crossed with the proprietary *Petunia* seedling 'PH-2013-4418', which displayed blue flowers having a white spotted flower color pattern. 'PH-2013-4418' resulted from a cross between 'PH-2012-3528' and the solid-orange-red colored variety HEADLINER 'Electric Orange' ('KLEPH14249'). Among the progeny of the cross between 'PH-2013-4407 and 'PH-2013-4418', the inventors selected the seedling 'PH-2014-0439', which displayed red flowers having a white spotted flower color pattern. A further cross of 'PH-2014-0439', with the commercial *Petunia* variety 'Viva Bright Red' produced the variety 'PH-2016-2068', which displays flowers having a white spotted flower color pattern on a red star pattern in combination with a white base petal color.

As shown in FIG. 7, the spots vary from circular to irregular shape, vary in size, and are present on at least one petal of the flower.

8. Breeding of the Line 'PH-2015-1080' (FIG. 8)

Figure 8:
FIG. 8 is a photo showing a close-up of an individual flower of proprietary *Petunia* line 'PH-2015-1080' showing white spots on a pink base petal color.

*Petunia* line 'PH-2015-1080', as shown in FIG. 8, displays flowers having a white spotted flower color pattern on a pink base petal color and is the result of a planned breeding program. In 2012, PH-2012-3528', which was the first seedling discovered by Applicant showing the novel spotted flower color pattern, was crossed with the proprietary *Petunia* seedling 'PH-2011-2416', which had solid-red flowers. The resulting progeny from this cross, 'PH-2013-4407', displayed purple flowers having a white spotted flower color pattern. 'PH-2013-4407' was further crossed with the proprietary *Petunia* seedling 'PH-2013-4418' which displayed blue flowers having a white spotted flower color pattern. 'PH-2013-4418' resulted from a cross between 'PH-2012-3528' and the solid-orange-red colored variety HEADLINER 'Electric Orange' ('KLEPH14249'). Among the progeny of the cross between 'PH-2013-4407' and 'PH-2013-4418', the inventors selected the seedling 'PH-2014-0443', which displayed dark-pink flowers having a white spotted flower color pattern. A further cross of 'PH-2014-0443' with the commercial *Petunia* variety STARLET 'Magenta' ('KLEPH15254') produced the variety 'PH-2015-1080', which shows flowers having a white spotted flower color pattern on a pink base petal color.

As shown in FIG. 8, the spots vary from circular to irregular shape, vary in size, and are present on at least one petal of the flower.

9. Further Features of the Spotted Flower Color Pattern

The size and diameter of the spots may vary from 1 mm up to 1 cm in diameter and may measure anywhere in between. The shape may be round or irregular. Further, the border of the spots may be clear or indistinct. Any of these characteristics can be shown in FIGS. 1-8.

Furthermore, the spotted flower color pattern may appear in combination with other color patterns, e.g. star pattern, border pattern or centers (Please see FIGS. 4-7) or in combinations of more than two of these patterns.

The number of spots on the entire flower may vary up to several hundred spots. If the spotted flower color pattern is combined with another color pattern, the number of respective spots may reduce accordingly to the size of the respective spotted area. *Petunia* flower size was measured for several-hundred progeny having the spotted flower color pattern. *Petunia* flower sizes may vary from 2.5 cm to 10.5 cm in diameter.

Additionally, the novel spotted flower color pattern may appear on single flowers with five petals, which may or may not be fused, or, alternatively it may emerge on double-flowering inflorescences having more than five petals.

Furthermore, the spotted flower color pattern may emerge on plants having an upright habit, as well as on plants having a spreading habit. Further, the vigor of the *Petunia* plants showing the unique spotted flower color pattern may vary from very compact to very vigorous.

The *Petunia* plants with the unique color pattern can be used as pot plants, container plants or in window boxes as well as in the field.

References to Known Patent Status of Referenced *Petunia* Varieties

The known patent status of the several above-referenced varieties are as follows: 'PH-2012-3528', 'PH-2015-1118', 'PH-2015-1132', 'PH-2011-2416', 'PH-2013-4418', 'KLEPH08153', 'Duesurmidco', and 'KLEPH14250' are unpatented; the patent status of 'Can Can' is unknown; the U.S. patent number of KLEPH15245 is USPP27,310; the U.S. patent number of KLEPH14249 is USPP27,431; the U.S. patent number of KLEPH15313 is USPP27,237; and the U.S. patent number of 'Duesurmar' is USPP21,673.

10. Molecular Background of the Spotted Flower Color Pattern in *Petunia*

The *Petunia* variety 'Can Can' as mentioned above exhibits a bicolor color pattern similar to other star-type *Petunias*. In this group (of star-type *Petunia*), it was shown that the pattern is induced by sequence-specific RNA degradation of Chalcone Synthase, the first specific enzyme in anthocyanin pigment biosynthesis. Please see Morita, Y., et al. "Tandemly arranged chalone synthase A genes contribute to the spatially regulated expression in siRNA and the natural bicolor floral phenotype in *Petunia* hybrida" *The Plant Journal.* 70:739-749 (2012). Sequence-specific RNA degradation occurs during a process called post-transcriptional gene silencing (PTGS) which protects the cell from viral infection. PTGS is triggered by over threshold-levels of viral gene mRNA. Also, over threshold-amounts of plant gene mRNA can trigger PTGS. Please see Baulcombe, D. "RNA silencing in plants" *Nature.* 431:356-363 (2004).

To prove whether PTGS is also responsible for the spotted flower color pattern in the claimed spotted *Petunia* plants of the present application that were derived from 'Can Can', 'KLEPH15313' was subjected to infection with cucumber mosaic virus (CMV). This virus is known to encode a protein, which suppresses PTGS by preventing translocation of the silencing signal. Please see Baulcombe, D. "Viral suppression of systemic silencing" *Trends Microbiol.* 10:306-308 (2002). The result is a strong reduction or total loss of white petal areas on star-type *Petunia* flowers. Please see Koseki, M., et al. "The star-type color pattern in *Petunia* hybrida 'Red Star' flowers is induced by sequence-specific degradation of chalcone synthase RNA" *Plant Cell Physiol.* 46: 1879-1883 (2005).

Three CMV isolates were selected for infection, because they caused severe symptoms on *Nicotiana benthamiana*: isolate PV-0506 of subgroup IB lead to stunted plant growth, isolate PV-0474 of subgroup IB triggered leaf deformations with shoestring leaves, isolate PV-0036 of subgroup IA induced severe chlorosis on infected *N. benthamiana* plants. RNAs of the three isolates were extracted, transcribed, amplified and successfully cloned into the pCB vector pDIVA3. With *Agrobacterium tumefaciens* bacteria, the cloned RNAs could be propagated and infiltrated in *N. benthamiana* plants. The cloned RNAs were part of the vector T-DNAs that were transferred by the bacteria into plant cells in which the viral genes were transiently expressed. Crude leaf extracts containing the CMV particles of one of the isolates each was used to inoculate *Petunia* plants by carborundum treatment.

CMV Infection of *Petunia* Variety 'KLEPH15313'

The three clones of PV-0506, PV-0474 and PV-0036 successfully inoculated *Petunia* x *hybrida* plants of variety 'KLEPH15313'. Twenty *Petunia* plants (four-weeks old) were inoculated per clone. As negative controls, 12 *Petunia* plants were mock inoculated only with buffer and 12 *Petunia* plants were left untreated. Plants were kept in greenhouse and symptom development was observed Plants infected with clone PV-0506 were affected in growth and displayed some chlorosis as well as necrosis. Plants and flowers were slightly smaller than healthy plants and flowers. Additionally, most of the flowers were completely purple (FIG. 9 D) or had a purple smear in the white petal tips (FIG. 9 C). Some flowers had an unaltered appearance. Plants inoculated with clone PV-0474 looked healthy. In plant size and growth, they resembled the mock and untreated plants. Flower number and size was also unchanged, but there were some changes in flower appearance. While the plants produced mostly normal flower types (FIGS. 9 A and B), there were a few purple flowers having white petal tips and purple "smears" with vanishing white dots (FIG. 9C) that were produced, and some flowers were completely purple (FIG. 9D). The clone of isolate PV-0036 caused severe symptoms with necrosis and chlorosis of leaves producing a dark green dot pattern on light green leaves (FIG. 9E). Plants and flowers were smaller in size and the majority of flowers were completely purple (FIG. 9D).

Comparative CMV Infection of *Petunia* Flowers with Different Color Patterns

Three additional *Petunia* flower pattern types were infected with clone PV-0506 as described above: line PH-2014-0028', exhibiting a star pattern-type flower, line 'PH-2007-0103', exhibiting a Picotee flower pattern with solid white border pattern, and line 'PH-2015-1874' described above, which has a solid border pattern in combination with the spotted flower color pattern. Six plants each were CMV-infected, and 4 plants of each line served as a negative control. Plants were cultivated in a greenhouse and evaluated 4 weeks after mechanical infection as described above.

Infected plants and flowers of line 'PH-2014-0028' were smaller than healthy plants and flowers and showed some necrosis. Additionally, all flowers of this infected line lost the star-pattern flower and were completely purple (FIGS. 10 A3 and A4). This in accordance with earlier observations on CMV-infected star-type flower pattern (Koseki, 2005) and validates this PTGS inhibition experiment. Similarly, infected plants of line 'PH-2007-0103' showed retarded growth, but with only some necrosis and no chloroses. Plants and flowers were a bit smaller than healthy plants and flowers. But in contrast to line 'PH-2014-0028', flowers retained their white margin unaffected (FIGS. 10B3 and 10B4). Finally, line 'PH-2015-1874' showed dwarfed plants and smaller flower size upon infection. Flowers exhibited vanishing white dots or a total loss of white dots, whereas the white margin remained unaffected (FIGS. 10C3 and 10C4).

These experiments clearly document that the appearance of spotted flower color pattern originates from PTGS in single, stochastically (randomly) distributed cells and the spread of the PTGS signal to adjacent cells. When the translocation of the silencing signal is prevented by viral interaction, the white spots or dots vanish until complete disappearance. The same mechanism has been proposed for star-pattern *Petunia* (See Koseki et a. 2005), however the phenotype of white spots or dots was unexpected and not previously shown. The formation of a white flower margin as in Picotee line 'PH-2007-0103' originates from a molecular mechanism different from PTGS.

Expression Analysis of the Chalcone Synthase A Gene

To further investigate the molecular background of the spotted flower color pattern, a comparative expression analysis was performed on the first specific step in anthocyanin biosynthesis, the Chalcone Synthase A gene. This key gene has been shown before to be the target of PTGS in white petal areas (Koseki et al. 2005, Morita et al. 2012). For primer generation, publicly available sequences of the *Petunia* x *hybrida* Chalcone Synthase A gene were aligned. The deduced consensus sequence resulted in Primer CHSA-for (SEQ ID NO:1) and CHSA-rev (SEQ ID NO:2), respectively. Total RNA was isolated using INVITRAP® Spin Plant RNA Mini Kit (Stratek, Germany) according to the manufacturer's instructions. cDNA was subsequently generated using the M-MLV Reverse Transcriptase Kit (Promega, USA) according to the manufacturer's instructions. The PCR-Reaction for Actin or Chalcone Synthase A genes contained in a final volume reaction of 25 µL: 1 µL of cDNA as a template, 2 µL of 10×PCR Buffer, 1.2 µL of $MgCl_2$, 0.2 µL of dNTP mix (10 mM each), 0.5 µL of each specific primer (10 pmol) and 0.2 µL of Taq Polymerase. The cycling conditions were an initial denaturation at 95° C. for 3 minutes; 30 cycles of 95° C. for 30 seconds, 55° C. for 30 seconds and 72° C. for 30 seconds; and a final extension at 72° C. for 10 minutes. PCR products were visualized in a 2% (w/v) agaroses gel, at 120 W for 90 minutes.

Figure 11:
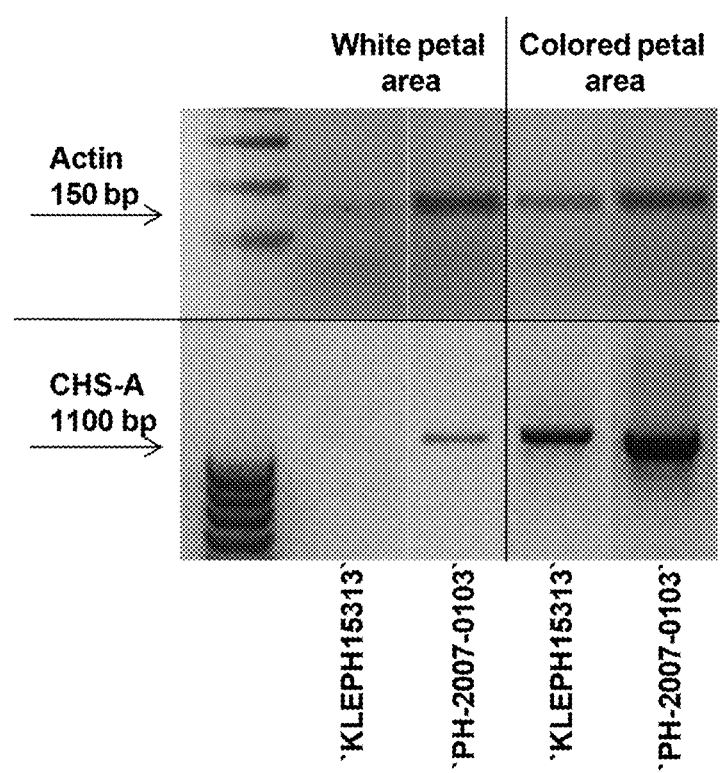
FIG. 11 shows the expression analysis of Chalcone Synthase A gene (CHS-A) from RNA of white and colored petal areas of *Petunia* x *hybrida* variety 'KLEPH15313' and Picotee-patterned line 'PH-2007-0103'. Expression of the actin gene was used as internal control.

FIG. 11 shows the results, that Chalcone Synthase A (CHS-A) expression cannot be observed in white petal tissue of variety 'KLEPH15313', whereas it can clearly be detected in white petal tissue of line 'PH-2007-0103' (FIG. 11). This supports the hypothesis that the white spots or dots and areas in 'KLEPH15313' originate from single, stochastically (randomly) distributed petal cells in which Chalcone Synthase, the first specific step in anthocyanin biosynthesis, has been knocked down by PTGS. The white spots or dots become visible by subsequent spread of the silencing signal to adjacent petal cells and their final size is determined by the extent of this spread. This molecular mechanism is unexpected and different from the Picotee-type *Petunia* flowers, where the white margin area tissue is not influenced by PTGS and exhibits Chalcone Synthase A activity (See FIG. 11).

11. Intergeneric Breeding of the *Petunia* Plants Having the Spotted Flower Color Pattern with *Calibrachoa*

*Petunia* plants herein exhibiting the spotted flower color pattern may be bred with *Calibrachoa* plants to produce *Petunia-Calibrachoa* hybrid plants exhibiting the spotted flower color pattern. Such intergeneric breeding is well-known in the art.

FURTHER EMBODIMENTS

Breeding with *Petunia*

The goal of ornamental plant breeding is to develop new, unique and superior ornamental varieties and hybrids. The breeder initially selects and crosses two or more parental lines, followed by repeated crossing and selfing, producing many new genetic combinations. The breeder can theoretically generate billions of different genetic combinations via crossing, selection, selfing and mutations. Therefore, a breeder will never develop the same variety genetically and having the same traits from the exact same parents.

Each year, the plant breeder selects the germplasm to advance to the next generation. This germplasm is grown under unique and different geographical, climatic and soil conditions and further selections are then made during and at the end of the growing season. The varieties that are developed are unpredictable because the breeder's selection occurs in unique environments with no control at the DNA level, and with millions of different possible genetic combinations being generated. A breeder of ordinary skill in the art cannot predict the final resulting lines he develops, except possibly in a very gross and general fashion. The same breeder cannot produce the same variety twice by using the same original parents and the same selection techniques. This unpredictability results in the expenditure of large amounts of research monies to develop superior new *Petunia* varieties.

Breeding programs combine desirable traits from two or more varieties or various broad-based sources into breeding pools from which varieties are developed by further crossing or selfing and selection of desired phenotypes. Pedigree breeding is used commonly for the improvement of self-pollinating plants. Two parents that possess favorable, complementary traits are crossed to produce an $F_1$. An $F_2$ population is produced by selfing one or several $F_1$s. Selection of the best individuals may begin in the $F_2$ population; then, beginning in the $F_3$, the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Using *Petunia* Plants Having a Spotted Flower Color Pattern to Develop Other *Petunia* Plants Having a Spotted Flower Color Pattern The *Petunia* plants herein can also provide a source of breeding material that may be used to develop new *Petunia* plants and varieties. Plant breeding techniques known in the art and used in a *Petunia* plant breeding program include, but are not limited to, recurrent selection, mass selection, bulk selection, hybridization, mass selection, backcrossing, pedigree breeding, open-pollination breeding, restriction fragment length polymorphism enhanced selection, genetic marker enhanced selection, making double haploids, mutagenesis and transformation. Often combinations of these techniques are used. There are many analytical methods available to evaluate a new variety. The oldest and most traditional method of analysis is the observation of phenotypic traits, but genotypic analysis may also be used.

Additional Breeding Methods

Any plants produced using the *Petunia* plants disclosed in the present application as at least one parent are also an embodiment. These methods are well-known in the art and some of the more commonly used breeding methods are described herein. Descriptions of breeding methods can be found in one of several reference books (e.g., Allard, "Principles of Plant Breeding" (1999); Vainstein, "Breeding for Ornamentals: Classical and Molecular Approaches," Kluwer Academic Publishers (2002); Callaway, "Breeding Ornamental Plants," Timber Press (2000); and Bragdø, Marie, "Inter-specific Crosses in Lupinus: Cytology and Inheritance of Flower Color," Institute of Genetics and Plant Breeding, Agricultural College of Norway, Vollebekk, Norway (Sep. 28, 1956).

Breeding steps that may be used in the *Petunia* plant breeding program can include for example, pedigree breeding, backcrossing, mutation breeding, and recurrent selection. In conjunction with these steps, techniques such as RFLP-enhanced selection, genetic marker enhanced selection (for example, SSR markers), and the making of double haploids may be utilized.

As used herein, the term "plant" includes plant cells, plant protoplasts, plant cell tissue cultures from which *Petunia* plants can be regenerated, plant calli, plant clumps, and plant cells that are intact in plants or parts of plants, such as pollen, ovules, embryos, protoplasts, meristematic cells, callus, leaves, anthers, cotyledons, hypocotyl, pistils, roots, root tips, seeds, flowers, petiole, shoot, or stems and the like.

Pedigree Breeding

Pedigree breeding starts with the crossing of two genotypes, such as *Petunia* spotted flower color pattern phenotype and another different *Petunia* having one or more desirable characteristics that is lacking or which complements the *Petunia* spotted flower color pattern phenotype. If the two original parents do not provide all the desired characteristics, other sources can be included in the breeding population. In the pedigree method, superior plants are selfed and selected in successive filial generations. In the succeeding filial generations, the heterozygous condition gives way to homogeneous varieties as a result of self-pollination and selection. Typically in the pedigree method of breeding, five or more successive filial generations of selfing and selection is practiced: $F_1$ to $F_2$; $F_2$ to $F_3$; $F_3$ to $F_4$; $F_4$ to $F_5$; etc. After a sufficient amount of inbreeding, successive filial generations will serve to increase seed of the developed variety. Preferably, the developed variety comprises homozygous alleles at about 95% or more of its loci.

Backcross Breeding

Backcross breeding has been used to transfer genes for a simply inherited, highly heritable trait into a desirable homozygous variety or inbred line which is the recurrent parent. The source of the trait to be transferred is called the donor parent. After the initial cross, individuals possessing the phenotype of the donor parent are selected and repeatedly crossed (backcrossed) to the recurrent parent. The resulting plant is expected to have the attributes of the recurrent parent and the desirable trait transferred from the donor parent.

In addition to being used to create a backcross conversion, backcrossing can also be used in combination with pedigree breeding. As discussed previously, backcrossing can be used to transfer one or more specifically desirable traits from one variety, the donor parent, to a developed variety called the recurrent parent, which has overall good commercial characteristics and yet lacks that desirable trait or traits. However, the same procedure can be used to move the progeny toward the genotype of the recurrent parent, but at the same time retain many components of the nonrecurrent parent by stopping the backcrossing at an early stage and proceeding with selfing and selection. For example, a *Petunia* plant may be crossed with another variety to produce a first-generation progeny plant. The first-generation progeny plant may then be backcrossed to one of its parent varieties to create a $BC_1$ or $BC_2$. Progeny are selfed and selected so that the newly developed variety has many of the attributes of the recurrent parent and yet several of the desired attributes of the nonrecurrent parent. This approach leverages the value and strengths of the recurrent parent for use in new *Petunia* varieties.

Therefore, another embodiment is a method of making a backcross conversion of the *Petunia* having the spotted flower color pattern, comprising the steps of crossing a *Petunia* plant having the spotted flower color pattern phenotype with a donor plant comprising a desired trait, selecting an $F_1$ progeny plant comprising the desired trait, and backcrossing the selected $F_1$ progeny plant to a plant of *Petunia* having the spotted flower color pattern phenotype. This method may further comprise the step of obtaining a molecular marker profile of *Petunia* having the spotted flower color pattern phenotype and using the molecular marker profile to select for a progeny plant with the desired trait and the molecular marker profile of *Petunia* having the spotted flower color pattern phenotype.

Recurrent Selection and Mass Selection

Recurrent selection is a method used in a plant breeding program to improve a population of plants. *Petunia* having the spotted flower color pattern phenotype are suitable for use in a recurrent selection program. The method entails individual plants cross-pollinating with each other to form progeny. The progenies are grown and the superior progenies selected by any number of selection methods, which include individual plant, half-sib progeny, full-sib progeny, and selfed progeny. The selected progenies are cross-pollinated with each other to form progeny for another population. This population is planted and again superior plants are selected to cross-pollinate with each other. Recurrent selection is a cyclical process and therefore can be repeated as many times as desired. The objective of recurrent selection is to improve the traits of a population. The improved population can then be used as a source of breeding material to obtain new varieties for commercial or breeding use, including the production of a synthetic variety. A synthetic variety is the resultant progeny formed by the intercrossing of several selected varieties.

Mass selection is a useful technique when used in conjunction with molecular marker enhanced selection. In mass selection, seeds from individuals are selected based on phenotype or genotype. These selected seeds are then bulked and used to grow the next generation. Bulk selection requires growing a population of plants in a bulk plot, allowing the plants to self-pollinate, harvesting the seed in bulk, and then using a sample of the seed harvested in bulk to plant the next generation. Also, instead of self-pollination, directed pollination could be used as part of the breeding program.

Mass and recurrent selections can be used to improve populations of either self- or cross-pollinating plants. A genetically variable population of heterozygous individuals is either identified, or created, by intercrossing several different parents. The best plants are selected based on individual superiority, outstanding progeny, or excellent combining ability. The selected plants are intercrossed to produce a new population in which further cycles of selection are continued.

Mutation Breeding

Mutation breeding is another method of introducing new traits into *Petunia* having the spotted flower color pattern phenotype. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g., cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil)), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques. Details of mutation breeding can be found in Vainstein, "Breeding for Ornamentals: Classical and Molecular Approaches," Kluwer Academic Publishers (2002). In addition, mutations created in other *Petunia* plants may be used to produce a backcross conversion of *Petunia* having the spotted flower color pattern phenotype that comprises such mutation.

Additional methods include, but are not limited to, expression vectors introduced into plant tissues using a direct gene transfer method, such as microprojectile-mediated delivery, DNA injection, electroporation, and the like. More preferably, expression vectors are introduced into plant tissues by using either microprojectile-mediated delivery with a biolistic device or by using *Agrobacterium*-mediated transformation. Transformant plants obtained with the protoplasm of the subject *Petunia* plants are intended to be within the scope of the embodiments of the application.

Single-Gene Conversions

When the term *Petunia* plant is used in the context of an embodiment of the present application, this also includes any single gene conversions of *Petunia* having the spotted flower color pattern phenotype. The term single gene converted plant as used herein refers to those *Petunia* plants which are developed by a plant breeding technique called backcrossing wherein essentially all of the desired morphological and physiological characteristics of a variety are recovered in addition to the single gene transferred into the variety via the backcrossing technique. Backcrossing methods can be used with one embodiment of the present application to improve or introduce a characteristic into the variety. The term "backcrossing" as used herein refers to the repeated crossing of a hybrid progeny back to the recurrent parent, i.e., backcrossing 1, 2, 3, 4, 5, 6, 7, 8, or more times to the recurrent parent. The parental *Petunia* plant that contributes the gene for the desired characteristic is termed the nonrecurrent or donor parent. This terminology refers to the fact that the nonrecurrent parent is used one time in the backcross protocol and therefore does not recur. The parental *Petunia* plant to which the gene or genes from the nonrecurrent parent are transferred is known as the recurrent parent as it is used for several rounds in the backcrossing protocol (Poehlman & Sleper (1994). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a *Petunia* plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original variety. To accomplish this, a single gene of the recurrent variety is modified or substituted with the desired gene from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially important trait or traits to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new variety but that can be improved by backcrossing techniques. These traits are well-known in the art.

Introduction of a New Trait or Locus into *Petunia* Having the Spotted Flower Color Pattern Phenotype

*Petunia* having the spotted flower color pattern phenotype represent a new base of genetics into which a new locus or trait may be introgressed. Direct transformation and backcrossing represent two important methods that can be used to accomplish such an introgression. The term backcross conversion and single locus conversion are used interchangeably to designate the product of a backcrossing program.

Backcross Conversions of *Petunia* Having the Spotted Flower Color Pattern Phenotype A backcross conversion of *Petunia* having the spotted flower color pattern phenotype occurs when DNA sequences are introduced through backcrossing (Allard, "Principles of Plant Breeding" (1999) with *Petunia* having the spotted flower color pattern phenotype utilized as the recurrent parent. Both naturally occurring and transgenic DNA sequences may be introduced through backcrossing techniques. A backcross conversion may produce a plant with a trait or locus conversion in at least two or more backcrosses, including at least 2 crosses, at least 3 crosses, at least 4 crosses, at least 5 crosses, and the like. Molecular marker assisted breeding or selection may be utilized to reduce the number of backcrosses necessary to achieve the backcross conversion. For example, see, Openshaw, S. J., et al., Marker-assisted Selection in Backcross Breeding, Proceedings Symposium of the Analysis of Molecular Data, *Crop Science Society of America*, Corvallis, Oreg. (August 1994), where it is demonstrated that a backcross conversion can be made in as few as two backcrosses.

The complexity of the backcross conversion method depends on the type of trait being transferred (single genes or closely linked genes as compared to unlinked genes), the level of expression of the trait, the type of inheritance (cytoplasmic or nuclear), and the types of parents included in the cross. It is understood by those of ordinary skill in the art that for single gene traits that are relatively easy to classify, the backcross method is effective and relatively easy to manage. See, Allard, "Principles of Plant Breeding" (1999). Desired traits that may be transferred through backcross conversion include, but are not limited to, sterility (nuclear and cytoplasmic), fertility restoration, drought tolerance, nitrogen utilization, ornamental features, disease resistance (bacterial, fungal, or viral), insect resistance, and herbicide resistance. In addition, an introgression site itself, such as an FRT site, Lox site, or other site specific integration site, may be inserted by backcrossing and utilized for direct insertion of one or more genes of interest into a specific plant variety. In some embodiments, the number of loci that may be backcrossed into *Petunia* having the spotted flower color pattern phenotype is at least 1, 2, 3, 4, or 5, and/or no more than 6, 5, 4, 3, or 2. A single locus may contain several transgenes, such as a transgene for disease resistance that, in the same expression vector, also contains a transgene for herbicide resistance. The gene for herbicide resistance may be used as a selectable marker and/or as a phenotypic trait. A single locus conversion of site specific integration system allows for the integration of multiple genes at the converted loci.

The backcross conversion may result from either the transfer of a dominant allele or a recessive allele. Selection of progeny containing the trait of interest is accomplished by direct selection for a trait associated with a dominant allele. Transgenes or genes transferred via backcrossing typically function as a dominant single gene trait and are relatively easy to classify. Selection of progeny for a trait that is transferred via a recessive allele requires growing and selfing the first backcross generation to determine which plants carry the recessive alleles. Recessive traits may require additional progeny testing in successive backcross generations to determine the presence of the locus of interest. The last backcross generation is usually selfed to give pure breeding progeny for the gene(s) being transferred, although a backcross conversion with a stably introgressed trait may also be maintained by further backcrossing to the recurrent parent with selection for the converted trait.

Molecular Techniques Using *Petunia* Having the Spotted Flower Color Pattern Phenotype The advent of new molecular biological techniques has allowed the isolation and characterization of genetic elements with specific functions. Traditional plant breeding has principally been the source of new germplasm, however, advances in molecular technologies have allowed breeders to provide varieties with novel and much wanted commercial attributes. Molecular techniques such as transformation are popular in breeding ornamental plants and well-known in the art. See Vainstein, "Breeding for Ornamentals: Classical and Molecular Approaches," Kluwer Academic Publishers (2002).

Breeding with Molecular Markers

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the genome of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called genetic marker enhanced selection. Molecular markers may also be used to identify and exclude certain sources of germplasm as parental varieties or ancestors of a plant by providing a means of tracking genetic profiles through crosses. Molecular markers, which includes markers identified through the use of techniques such as Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs), and Single Nucleotide Polymorphisms (SNPs), may be used in plant breeding methods utilizing *Petunia* plants having the spotted flower color pattern phenotype. See Vainstein, "Breeding for Ornamentals: Classical and Molecular Approaches," Kluwer Academic Publishers (2002).

Genetic Marker Profile Through SSR and First Generation Progeny

In addition to phenotypic observations, a plant can also be identified by its genotype. The genotype of a plant can be characterized through a genetic marker profile which can identify plants of the same variety, or a related variety, or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) (which are also referred to as Microsatellites), and Single Nucleotide Polymorphisms (SNPs), all of which are well-known in the art.

Tissue Culture

Further reproduction of the variety can occur by tissue culture and regeneration. Tissue culture of various tissues of ornamental plants and *Petunia* and regeneration of plants therefrom is well-known and widely published. For example, reference may be had to do Valla Rego, Luciana et al., Crop Breeding and Applied Technology. 1(3): 283-300 (2001); Komatsuda, T., et al., *Crop Sci.*, 31:333-337 (1991); Stephens, P. A., et al., *Theor. Appl. Genet.*, 82:633-635 (1991); Komatsuda, T., et al., *Plant Cell, Tissue and Organ*

Culture, 28:103-113 (1992); Dhir, S., et al., *Plant Cell Reports*, 11:285-289 (1992); Pandey, P., et al., *Japan J. Breed.*, 42:1-5 (1992); and Shetty, K., et al., *Plant Science*, 81:245-251 (1992). Thus, another embodiment is to provide cells which upon growth and differentiation produce *Petunia* plants having the physiological and morphological characteristics of *Petunia* described in the present application.

Regeneration refers to the development of a plant from tissue culture. The term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as pollen, ovules, embryos, protoplasts, meristematic cells, callus, leaves, anthers, cotyledons, hypocotyl, pistils, roots, root tips, flowers, seeds, petiole, shoot, or stems, and the like. Means for preparing and maintaining plant tissue culture are well-known in the art.

Targeted Gene Editing

Targeted gene editing can be done using CRISPR/Cas9 technology (Saunders & Joung, *Nature Biotechnology*, 32, 347-355, 2014). CRISPR is a type of genome editing system that stands for Clustered Regularly Interspaced Short Palindromic Repeats. This system and CRISPR-associated (Cas) genes enable organisms, such as select bacteria and archaea, to respond to and eliminate invading genetic material. Ishino, Y., et al. *J. Bacteriol.* 169, 5429-5433 (1987). These repeats were known as early as the 1980s in *E. coli*, but Barrangou and colleagues demonstrated that *S. thermophilus* can acquire resistance against a bacteriophage by integrating a fragment of a genome of an infectious virus into its CRISPR locus. Barrangou, R., et al. *Science* 315, 1709-1712 (2007). Many plants have already been modified using the CRISPR system. See for example, U.S. Application Publication No. WO2014068346 (György et al., Identification of a *Xanthomonas euvesicatoria* resistance gene from pepper (*Capsicum annuum*) and method for generating plants with resistance), Martinelli, F. et al., "Proposal of a Genome Editing System for Genetic Resistance to Tomato Spotted Wilt Virus" *American Journal of Applied Sciences* 2014, and Noman, A. et al., "CRISPR-Cas9: Tool for Qualitative and Quantitative Plant Genome Editing" *Frontiers in Plant Science* Vol. 7 November 2016.

Gene editing can also be done using crRNA-guided surveillance systems for gene editing. Additional information about crRNA-guided surveillance complex systems for gene editing can be found in the following documents, which are incorporated by reference in their entirety: U.S. Application Publication No. 2010/0076057 (Sontheimer et al., Target DNA Interference with crRNA); U.S. Application Publication No. 2014/0179006 (Feng, CRISPR-CAS Component Systems, Methods, and Compositions for Sequence Manipulation); U.S. Application Publication No. 2014/0294773 (Brouns et al., Modified Cascade Ribonucleoproteins and Uses Thereof); Sorek et al., *Annu. Rev. Biochem.* 82:273-266, 2013; and Wang, S. et al., *Plant Cell Rep* (2015) 34: 1473-1476. Therefore, it is another embodiment to use the CRISPR system on the *Petunia* plants of the instant application to for example, modify traits and tolerances to pests and viruses.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions, and sub-combinations as are within their true spirit and scope.

One or more aspects may be embodied in other specific forms without departing from its spirit or essential characteristics. The described embodiments are to be considered in all respects only as illustrative and not restrictive. The scope of the embodiments is, therefore, indicated by the appended claims rather than by the foregoing description. All changes which come within the meaning and range of equivalency of the claims are to be embraced within their scope. The foregoing discussion of the embodiments has been presented for purposes of illustration and description. The foregoing is not intended to limit the embodiments to the form or forms disclosed herein. In the foregoing Further Embodiments, for example, various features of the embodiments are grouped together in one or more embodiments for the purpose of streamlining the disclosure. This method of disclosure is not to be interpreted as reflecting an intention that the claimed embodiments require more features than are expressly recited in each claim. Rather, as the following claims reflect, inventive aspects lie in less than all features of a single foregoing disclosed embodiment. Thus, the following claims are hereby incorporated into this Further Embodiments, with each claim standing on its own as a separate preferred embodiment.

Moreover, though the description of the embodiments has included description of one or more embodiments and certain variations and modifications, other variations and modifications are within the scope of the embodiments (e.g., as may be within the skill and knowledge of those in the art, after understanding the present disclosure). It is intended to obtain rights which include alternative embodiments to the extent permitted, including alternate, interchangeable and/or equivalent structures, functions, ranges or acts to those claimed, whether or not such alternate, interchangeable and/or equivalent structures, functions, ranges or acts are disclosed herein, and without intending to publicly dedicate any patentable subject matter.

The use of the terms "a," "an," and "the," and similar referents in the context of describing the embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the embodiments unless otherwise claimed. No language in the specification should be construed as indicating any non-claimed element as essential to the practice one or more embodiments.

DEPOSIT INFORMATION

Representative samples of proprietary *Petunia* tissue of the Klemm+Sohn GmbH & Co. KG comprising at least one dominant allele that produces a spotted flower color pattern, and wherein said *Petunia* plants grown from said tissue express a spotted flower color pattern, were made with the Provasoli-Guillard National Center for Marine Algae and Microbiota, Bigelow Laboratory for Ocean Sciences (NCMA), 60 Bigelow Drive, East Boothbay, Me. 04544. Variety 'KLEPH15313' was deposited May 10, 2018 and assigned NCMA Accession No. 201805004. Variety 'PH-2015-1874' was deposited Aug. 16, 2019 and assigned NCMA Accession No. 201908001. Variety 'PH-2014-0040' was deposited Jan. 19, 2022 and assigned NCMA Accession No. 202201008. Variety 'PH-2014-0443' was deposited Jan. 19, 2022 and assigned NCMA Accession No. 202201009. The deposits of plant tissue were taken from the same deposits maintained by Klemm+Sohn GmbH & Co. KG since prior to the filing date of this application. All claimed deposits were made pursuant to the Budapest treaty, and subject to the rules and regulations thereof. For the sake of clarity, Applicant affirmatively states the following: Upon issuance of a patent, all restrictions on the availability to the public of the deposit will be irrevocably removed consistent with all of the requirements of 37 C.F.R. §§ 1.801-1.809. The deposit will be maintained in the depository for a period of thirty years, or five years after the last request, or for the enforceable life of the patent, whichever is longer, and will be replaced as necessary during the period.

0040,' representative tissue of 'PH-2014-0040' having been deposited under NCMA No. 202201008, 'PH-2014-0443,' representative tissue of 'PH-2014-0443' having been deposited under NCMA No. 202201099, and 'PH-2015-1874,' representative tissue of 'PH-2015-1874' having been deposited under NCMA No. 201908001.

2. A method for producing a seed that develops into a *Petunia* plant having a spotted flower color pattern comprising one or more spots on one or more petals of a flower, said method comprising:

crossing a first *Petunia* plant with a stock *Petunia* plant, thereby producing the seed that develops into the *Petunia* plant having the spotted flower color pattern comprising one or more spots on one or more petals of a flower;

wherein the first *Petunia* and/or the stock *Petunia* plant has the spotted flower color pattern and is a product of applying a plant breeding technique to a parental line plant having the spotted flower color pattern; wherein the parental line plant is selected from the group consisting of: 'KLEPH15313,' representative tissue of 'KLEPH15313' having been deposited under NCMA No. 201805004, 'PH-2014-0040,' representative tissue of 'PH-2014-0040' having been deposited under NCMA No. 202201008, 'PH-2014-0443,' representa-

What is claimed is:

1. A method for producing a seed that develops into a *Petunia* plant having a spotted flower color pattern comprising one or more spots on one or more petals of a flower, said method comprising:

crossing a first *Petunia* plant with a stock *Petunia* plant and harvesting resulting seed, thereby producing the seed that develops into the *Petunia* plant having the spotted flower color pattern comprising one or more spots on one or more petals of a flower;

wherein the first *Petunia* plant and/or the stock *Petunia* plant has the spotted flower color pattern, and is a product of one or more crosses comprising a cross between: a parental line plant with another *Petunia* plant, or with itself; wherein the parental line plant is selected from the group consisting of: 'KLEPH15313,' representative tissue of 'KLEPH15313' having been deposited under NCMA No. 201805004, 'PH-2014- tive tissue of 'PH-2014-0443' having been deposited under NCMA No. 202201009, and 'PH-2015-1874,' representative tissue of 'PH-2015-1874' having been deposited under NCMA No. 201908001.

3. The method of claim 2, wherein said plant breeding technique is recurrent selection.

4. The method of claim 2, wherein said plant breeding technique is mass selection.

5. The method of claim 2, wherein said plant breeding technique is hybridization.

6. The method of claim 2, wherein said plant breeding technique is open-pollination.

7. The method of claim 2, wherein said plant breeding technique is backcrossing.

8. The method of claim 2, wherein said plant breeding technique is pedigree breeding.

9. The method of claim 2, wherein said plant breeding technique is mutation breeding, and wherein said mutation breeding selects for a mutation that is spontaneous or artificially induced.

10. The method of claim 2, wherein said plant breeding technique is marker enhanced selection.

11. A method for producing a seed that develops into a *Petunia* plant having a spotted flower color pattern comprising one or more spots on one or more petals of a flower, said method comprising:

selfing a stock *Petunia* plant, thereby producing the seed that develops into the *Petunia* plant having the spotted flower color pattern comprising one or more spots on one or more petals of a flower;

wherein the stock *Petunia* plant has the spotted flower color pattern and is a product of applying a plant breeding technique to a parental line plant having the spotted flower color pattern; wherein the parental line plant is selected from the group consisting of: 'KLEPH15313,' representative tissue of 'KLEPH15313' having been deposited under NCMA No. 201805004, 'PH-2014-0040,' representative tissue of 'PH-2014-0040' having been deposited under NCMA No. 202201008, 'PH-2014-0443,' representative tissue of 'PH-2014-0443' having been deposited under NCMA No. 202201009, and 'PH-2015-1874,' representative tissue of 'PH-2015-1874' having been deposited under NCMA No. 201908001.

12. The method of claim 11, wherein said plant breeding technique is recurrent selection.

13. The method of claim 11, wherein said plant breeding technique is mass selection.

14. The method of claim 11, wherein said plant breeding technique is hybridization.

15. The method of claim 11, wherein said plant breeding technique is open-pollination.

16. The method of claim 11, wherein said plant breeding technique is backcrossing.

17. The method of claim 11, wherein said plant breeding technique is pedigree breeding.

18. The method of claim 11, wherein said plant breeding technique is mutation breeding, and wherein said mutation breeding selects for a mutation that is spontaneous or artificially induced.

19. The method of claim 11, wherein said plant breeding technique is marker enhanced selection.

* * * * *

SEQUENCE LISTING

```
<160> NUMBER OF SEQ ID NOS: 2

<210> SEQ ID NO 1
<211> LENGTH: 23
<212> TYPE: DNA
<213> ORGANISM: Petunia x hybrida

<400> SEQUENCE: 1
atggtgacag tcgaggagta tcg                                        23

<210> SEQ ID NO 2
<211> LENGTH: 25
<212> TYPE: DNA
<213> ORGANISM: Petunia x hybrida

<400> SEQUENCE: 2
agttcctaaa ccttctttgg ctgag                                      25
```